United States Patent
Tsuda et al.

(10) Patent No.: US 10,772,581 B2
(45) Date of Patent: Sep. 15, 2020

(54) RADIATION TOMOGRAPH

(71) Applicant: Shimadzu Corporation, Kyoto (JP)

(72) Inventors: Tomoaki Tsuda, Kyoto (JP); Tetsuya Kobayashi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 359 days.

(21) Appl. No.: 15/776,926

(22) PCT Filed: Nov. 19, 2015

(86) PCT No.: PCT/JP2015/082606
§ 371 (c)(1),
(2) Date: May 17, 2018

(87) PCT Pub. No.: WO2017/085843
PCT Pub. Date: May 26, 2017

(65) Prior Publication Data
US 2020/0261031 A1    Aug. 20, 2020

(51) Int. Cl.
*A61B 6/03*    (2006.01)
*G06T 7/00*    (2017.01)

(52) U.S. Cl.
CPC ............ *A61B 6/037* (2013.01); *G06T 7/0012* (2013.01); *G06T 2207/10081* (2013.01); *G06T 2207/30004* (2013.01)

(58) Field of Classification Search
CPC .................. A61B 6/037; G06T 7/0012; G06T 2207/30004; G06T 2207/10081
See application file for complete search history.

(56) References Cited

U.S. PATENT DOCUMENTS

| 2014/0133728 A1 | 5/2014 | Blaffert et al. |
| 2015/0098640 A1 | 4/2015 | Berker et al. |
| 2015/0297168 A1* | 10/2015 | Panin ................ A61B 6/037 600/427 |

FOREIGN PATENT DOCUMENTS

| JP | 2007-086089 A | 4/2007 |
| JP | 2007-101341 A | 4/2007 |
| JP | 2014-520256 A | 8/2014 |
| JP | 2015-519555 A | 7/2015 |

OTHER PUBLICATIONS

International Search Report with English translation and Written Opinion dated Feb. 16, 2016 of corresponding International Application No. PCT/JP2015/082606; 7 pgs.

* cited by examiner

*Primary Examiner* — Said M Elnoubi
(74) *Attorney, Agent, or Firm* — Maier & Maier, PLLC

(57) ABSTRACT

A radiation tomograph whereby the acquisition of transmission data and the measurement of annihilation radiation pairs are simultaneously performed by a single detector ring so as to realize both reduction of the manufacturing cost of a PET device and reduction of a burden to a subject. The transmission data, which shows the distribution of annihilation radiation absorption characteristics within a subject, is computed from data relating to annihilation radiation pairs in the vicinity of a surface of the subject. The transmission data can be acquired by detecting a radioactive drug derived from the subject, which makes imaging exclusively for transmission data unnecessary.

8 Claims, 10 Drawing Sheets

Δt=0　　　　　　　　　　　Δt≠0

▨ DISTRIBUTION OF ABSORPTION
　CHARACTERISTIC OF RADIATION

▦ DISTRIBUTION OF DRUG

FIG.7
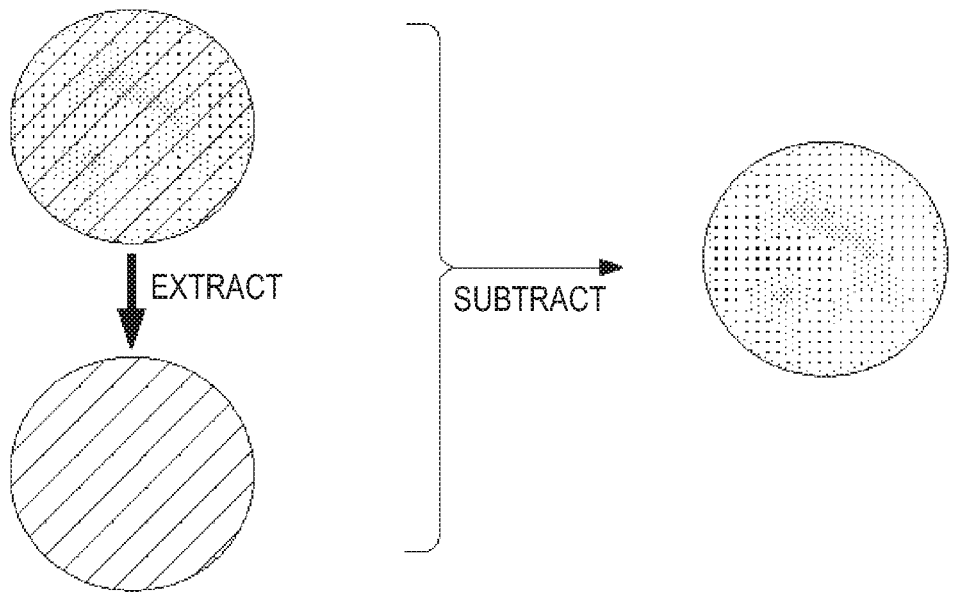
FIG.8
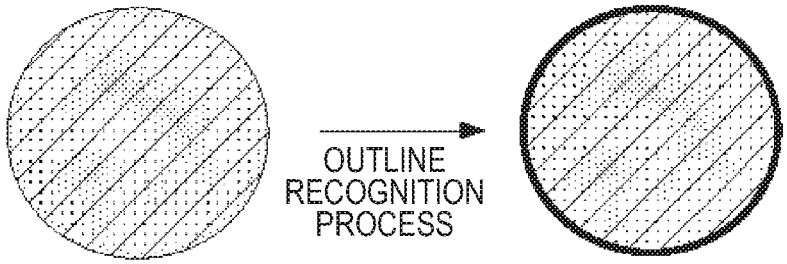
FIG.9
RAW DATA
| LOR | COUNT NUMBER |
|---|---|
| LOR 1 | 10000 |
| LOR 2 | 15000 |
| LOR 3 | 13000 |
| ⋮ | ⋮ |
→ SELECTION PROCESS
SELECTION DATA
| LOR | COUNT NUMBER |
|---|---|
| LOR 43 | 61000 |
| LOR 92 | 187000 |
| LOR 315 | 443000 |
| ⋮ | ⋮ |

RADIATION TOMOGRAPH

FIELD

The present invention relates to a radiation tomograph that detects an annihilation radiation pair radiated from a subject and performs imaging of a radioactive drug distribution in the subject, and particularly to a radiation tomograph having an absorption correction function.

BACKGROUND

A radiation tomograph for imaging a radioactive drug distribution is disposed in a medical institution. A description will be given of a specific configuration of such a radiation tomograph. A conventional radiation tomograph includes a detector ring in which radiation detectors for detecting radiation are arranged in an annular shape. This detector ring detects a pair of radiation rays (an annihilation radiation pair) in opposite directions irradiated from a radioactive drug in a subject (for example, see Patent Document 1).

A radiation tomograph for head inspection is present as a type of such a radiation tomograph. This head inspection imaging apparatus will be described in detail. FIG. 22 is a diagram for description of a conventional head inspection imaging apparatus. In the conventional head inspection imaging apparatus, a head of a subject is introduced into a detector ring 62 at the time of inspection. In this state, the detector ring 62 detects an annihilation radiation pair irradiated from the subject.

The detector ring 62 specifies a source of the annihilation radiation pair emitted from the head, and an image indicating a radioactive drug distribution is generated based on this position information. The radioactive drug has a property of gathering at a site at which amyloid accumulates, and thus dementia may be diagnosed when a radioactive drug distribution map is diagnosed.

Such a radiation tomograph has a problem that a generated image is unclear. Absorption of radiation in the head is a cause of disturbance of this image. The annihilation radiation pair generated in the head penetrates the head and is incident on the detector ring 62. The head has a characteristic of absorbing radiation to some extent. This absorption characteristic differs depending on the part of the head. Therefore, when a radioactive drug distribution image is attempted to be generated, a radiation absorption characteristic in the subject becomes uneven and is superimposed on the image.

Therefore, in the conventional radiation tomograph, an absorption characteristic (transmission data) of radiation in the head is measured, and a detection result of the detector ring 62 is corrected based on a result thereof (for example, see Patent Document 1). Such correction operation is referred to as an absorption correction. FIG. 23 illustrates a radiation tomograph having an absorption correction function. Transmission data is measured by generating radiation from a radiation source located outside a body of the subject. This detector ring 63 for acquisition of transmission data is different from the detector ring 62 for detection of an annihilation radiation pair emitted from the head. The mutual detector rings 62 and 63 are arranged adjacent to each other to use a central axis in common. A ring-shaped radiation source is disposed inside the detector ring 63.

Radiation generated from the ring-shaped radiation source is detected by the detector ring 63 for acquisition of transmission data across the head of the subject. When such radiation is detected, it is possible to obtain transmission data on the head. This transmission data represents unevenness of the absorption characteristic of radiation superimposed on the radioactive drug distribution image. Therefore, absorption correction can be performed based on the transmission data.

As a method of acquiring transmission data, in addition to a method described with reference to FIG. 23, one using a CT apparatus and an MRI apparatus in place of the detector ring 63 for acquisition of transmission data has been conceived.

Patent Document 1: JP-A-2007-086089

SUMMARY

However, the conventional radiation tomograph has a problem that an imaging apparatus for measuring transmission data is additionally needed.

In the apparatus illustrated in FIG. 23, the annihilation radiation pair in the head is measured by the detector ring 62, and the transmission data is acquired by the detector ring 63 for acquisition of transmission data. In this way, when two detector rings are disposed side by side, detection of radiation necessary for generating a clear distribution image can be executed in a flowing manner. However, since the number of detector rings is increased to measure transmission data, a manufacturing cost of the apparatus increases. Such a problem is the same when a CT apparatus and an MRI apparatus are added in place of the detector ring.

Then, a question whether it is impossible to complete detection of necessary radiation using only the detector ring 62 arises. Such a method is technically possible. That is, when transmission data is acquired while a subject and a radiation source are introduced into the detector ring 62, and then an annihilation radiation pair in the head is measured while the radiation source is separated from the detector ring 62, it is possible to complete detection of radiation necessary for generating a distribution image without providing a new detector ring.

However, in such a method, it is impossible to simultaneously perform acquisition of transmission data and measurement of an annihilation radiation pair. The detector ring 62 may not measure the annihilation radiation pair while acquiring the transmission data, and vice versa. That is, when it is attempted to complete detection of necessary radiation using only the detector ring 62, an imaging time is prolonged. Such circumstances are undesirable from a viewpoint of reducing a burden on the subject.

The invention has been made in view of the above circumstances, and an object of the invention is to provide a radiation tomograph capable of simultaneously performing acquisition of transmission data and measurement of an annihilation radiation pair using a single detector ring.

The invention adopts the following configurations to solve the above-mentioned problem.

That is, an information processing apparatus according to the invention is (P1) an information processing apparatus mounted in a radiation tomograph including a detector ring for detecting an annihilation radiation pair derived from a radioactive drug distributed in a subject, including (A) occurrence position specifying means for specifying an occurrence position of annihilation radiation based on a time difference when an annihilation radiation pair enters the detector ring and an incident position of the annihilation radiation pair on the detector ring, (B1) data selecting means for selecting data on a pair generated in a vicinity of a surface of the subject from data indicating an occurrence position of radiation specified by the occurrence position specifying means, (C1) absorption characteristic distribution computing means for computing absorption characteristic distribution data indicating a distribution of absorption characteristics of annihilation radiation inside the subject by computing a level of decrease of the number of times of detection of one of a pair scattering in a direction of penetrating the subject due to absorption in the subject based on the number of times of detection of radiation scattering in a tangential direction of a curved surface forming the surface of the subject in an annihilation radiation pair derived from the vicinity of the surface of the subject based on selected data, and (D) image generating means for generating an image indicating a radioactive drug distribution in the subject based on data indicating an occurrence position of radiation specified by the occurrence position specifying means, (E) wherein the image generating means generates an image by executing absorption correction based on the absorption characteristic distribution data.

[Effects] According to the invention, it is possible to realize both reduction of manufacturing cost of a positron emission tomography (PET) device and reduction of a burden on the subject by simultaneously performing acquisition of transmission data and measurement of the annihilation radiation pair using the single detector ring. The radiation imaging apparatus according to the invention is a TOF-PET, and may specify an occurrence position of annihilation radiation based on a time difference when an annihilation radiation pair enters the detector ring. The invention utilizes such a characteristic of the TOF-PET.

A greatest feature of the invention is to compute absorption characteristic distribution data (transmission data) indicating a distribution of absorption characteristics of annihilation radiation inside the subject from data on an annihilation radiation pair derived from the vicinity of the surface of the subject. In the TOF-PET, an occurrence position of a detected annihilation radiation pair is known, and thus it is possible to select data on the pair.

Conventional transmission data acquisition is performed by inserting a radiation source (external source) into a gap formed between the detector ring and the subject and transmitting radiation to the subject. The inventor of the invention thought that a radioactive drug administered to the subject could replace this radiation source without being bound by such technical common sense. The radioactive drug travels around the whole body of the subject, and thus is distributed to some extent on the surface of the subject. In this regard, an idea of using the radioactive drug accumulated on the surface of this subject in place of the conventional external source has been created.

According to the invention, since transmission data can be obtained by detection of the radioactive drug derived from the subject, imaging exclusively for transmission data is unnecessary. In this way, the detector ring dedicated to transmission data is not required, and it is unnecessary to take time for imaging exclusively for transmission data.

In addition, according to the invention, it is possible to obtain transmission data more suitable for absorption correction. In a conventional method using the external source, it is impossible to obtain transmission data faithfully representing an absorption distribution of a radioactive drug since energy of radiation emitted from the external source is different from energy of radiation emitted from the radioactive drug. According to the invention, transmission data is acquired by radiation derived from the radioactive drug, and thus it is possible to compute transmission data more faithfully showing a scheme in which radiation derived from the radioactive drug is absorbed.

In addition, in the information processing apparatus, it is more desirable that data selected by the data selecting means is related to an annihilation radiation pair derived from a radioactive drug accumulated in a capillary vessel under a skin of the subject.

The above-described configuration specifically specifies the vicinity of the surface of the subject used for computing the absorption characteristic distribution data. When data selected by the data selecting means is related to an annihilation radiation pair derived from a radioactive drug accumulated in a capillary vessel under a skin of the subject, it is possible to more reliably compute the absorption characteristic distribution data.

In addition, in the information processing apparatus, it is more desirable that the absorption characteristic distribution computing means operates by computing an absorption rate of radiation by dividing the number of times of detection of a pair scattering in the tangential direction of the curved surface forming the surface of the subject by the number of times of detection of a pair scattering in a direction of penetrating through the subject.

The above-described configuration describes a specific configuration of the invention. When an absorption rate of radiation is computed by dividing the number of times of detection of a pair scattering in the tangential direction of the curved surface forming the surface of the subject by the number of times of detection of a pair scattering in a direction of penetrating through the subject, it is possible to reliably obtain an absorption characteristic of annihilation radiation in the subject.

In addition, in the information processing apparatus, it is more desirable that the data selecting means operates based on data indicating a shape of an outline of the subject acquired in advance.

The above-described configuration describes a specific configuration of the invention. When there is valid data indicating the shape of the outline of the subject acquired in advance, the data selecting means may operate using the data.

In addition, an information processing apparatus according to the invention is (P2) an information processing apparatus mounted in a radiation tomograph including a detector ring for detecting an annihilation radiation pair derived from a radioactive drug distributed in a subject and a radiation source configured to irradiate radiation from an outside of the subject and disposed inside the detector ring, including (A) occurrence position specifying means for specifying an occurrence position of annihilation radiation based on a time difference when an annihilation radiation pair enters the detector ring and an incident position of the annihilation radiation pair on the detector ring, (B2) data selecting means for selecting data on a pair generated by the radiation source from data indicating an occurrence position of radiation specified by the occurrence position specifying means, (C2) absorption characteristic distribution computing means for computing absorption characteristic distribution data indicating a distribution of absorption characteristics of annihilation radiation in the subject based on selected data, and (D) image generating means for generating an image indicating a radioactive drug distribution in the subject based on data indicating an occurrence position of radiation specified by the occurrence position specifying means, (E) wherein the image generating means generates an image by executing absorption correction based on the absorption characteristic distribution data.

The above-described configuration describes another configuration in the invention. According to the invention, it is possible to realize both reduction of manufacturing cost of a PET device and reduction of a burden on the subject by simultaneously performing acquisition of transmission data and measurement of the annihilation radiation pair using the single detector ring.

The radiation imaging apparatus according to the invention is a TOF-PET, and may specify an occurrence position of annihilation radiation based on a time difference when an annihilation radiation pair enters the detector ring. The invention utilizes such a characteristic of the TOF-PET.

Conventional transmission data acquisition is performed by inserting a radiation source (external source) into a gap formed between the detector ring and the subject and transmitting radiation to the subject. Thereafter, the external source is separated from the detector ring, and detection of radiation derived from the radioactive drug distributed in the subject is performed this time to acquire emission data. The inventor of the invention thought whether not only transmission data but also emission data can be obtained in a state in which the external source is introduced without being bound by such technical common sense.

According to the invention, there is provided data selecting means capable of separating data related to radiation derived from the external source from data detected by the detector ring and generating transmission data. The data detected by the detector ring includes data on radiation derived from the radioactive drug in the subject. Therefore, when absorption correction using transmission data is performed on this data, it is possible to obtain a radioactive drug distribution image from which the absorption characteristic of the subject is eliminated.

According to the invention, it is possible to obtain a distribution image only by imaging using the external source without performing imaging twice under different conditions of having and not having the external source.

In addition, the invention is applicable to various apparatuses such as a radiation imaging apparatus for head imaging, etc.

According to the invention, it is possible to realize both reduction of a manufacturing cost of a PET device and reduction of a burden on a subject by simultaneously performing acquisition of transmission data and measurement of an annihilation radiation pair using a single detector ring. That is, transmission data indicating a distribution of an absorption characteristic of annihilation radiation in a subject is computed from data related to an annihilation radiation pair derived from the vicinity of a surface of the subject. According to the invention, transmission data may be obtained by detection of a radioactive drug derived from the subject, and thus it is unnecessary to perform imaging exclusively for the transmission data.

BRIEF DESCRIPTION OF THE DRAWINGS

FIG. 7 is a conceptual diagram for description of an overview of data processing according to Embodiment 1.

FIG. 8 is a schematic view for description of an outline extraction process according to Embodiment 1.

FIG. 9 is a schematic view for description of a data selection process according to Embodiment 1.

DETAILED DESCRIPTION OF THE DRAWINGS

Hereinafter, a description will be given of embodiments of a radiation tomograph according to the invention with reference to drawings. A γ-ray in Embodiment 1 is an example of radiation of the invention. A configuration of Embodiment 1 corresponds to an image diagnosis device for head inspection. That is, a radiation tomograph of Embodiment 1 is a type of a PET device that generates a tomographic image by imaging a radioactive drug distributed in a head. A radiation imaging apparatus for head inspection is an example of the embodiment. The invention may be applied to a radiation tomograph having another configuration such as a whole-body apparatus, a breast examination apparatus, etc. In addition, it is presumed that the invention corresponds to an apparatus related to a TOF-PET described below. An annihilation radiation pair emitted from the radioactive drug has energy of 511 kev.

Embodiment 1

Figure 1:
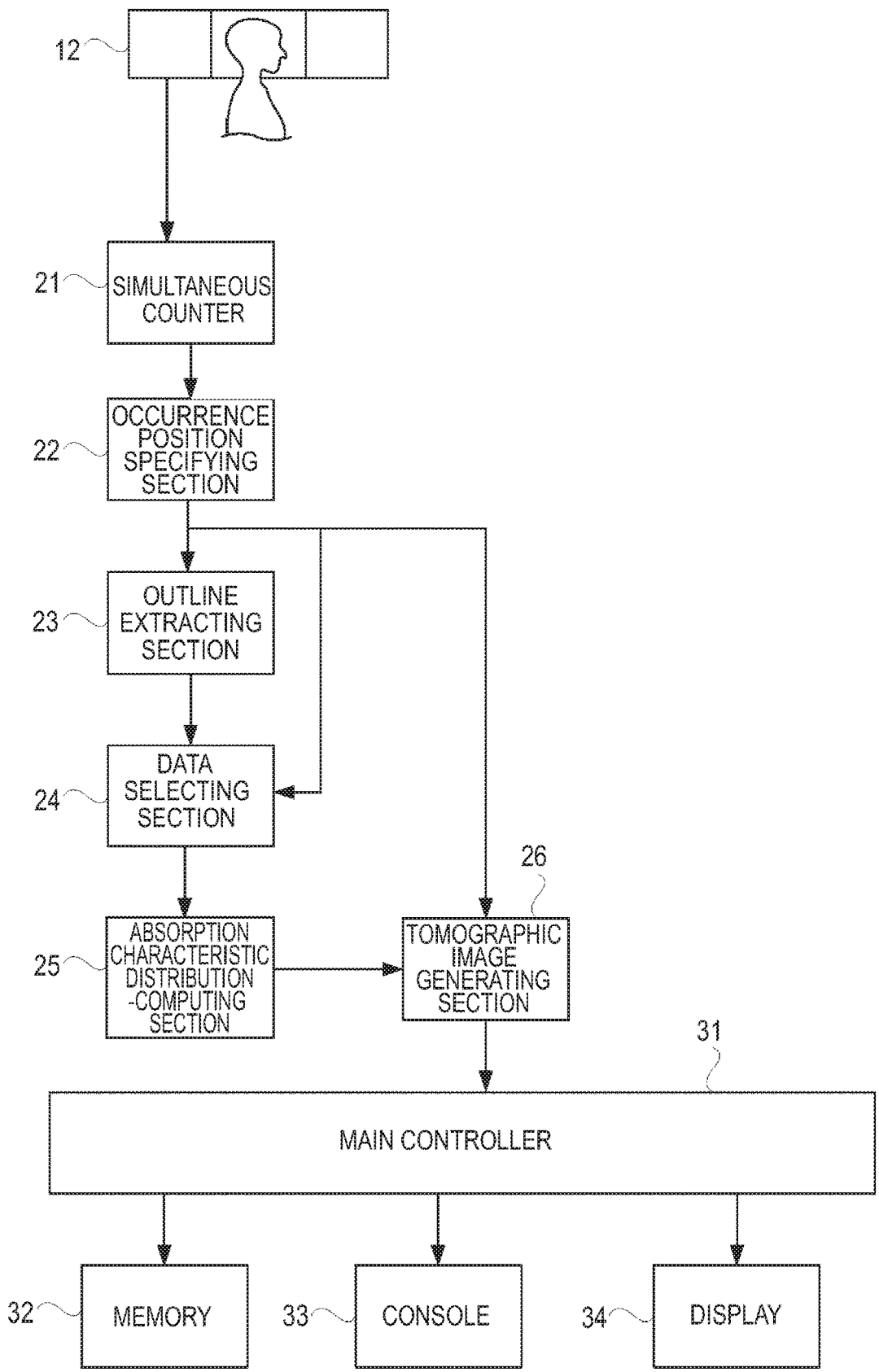
FIG. 1 is a functional block diagram for description of a radiation tomograph according to Embodiment 1.

FIG. 1 is a functional block diagram of a radiation tomograph according to the invention. That is, an apparatus according to the invention includes a detector ring 12 for introducing a head of a subject to which a positron emission type radioactive drug is administered, and respective sections 21, 22, 23, 24, and 25 related to information processing. The detector ring 12 is configured in a ring shape having a vertical central axis and configured to detect an annihilation radiation pair derived from a radioactive drug distributed in the head of the subject. In this specification, the respective sections related to information processing are collectively referred to as an information processing apparatus.

Figure 2:
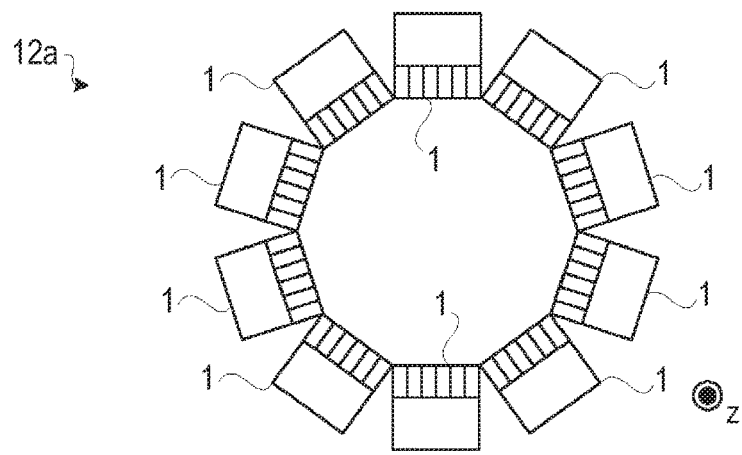
FIG. 2 is a plan view for description of a detector ring according to Embodiment 1.

A configuration of the detector ring 12 will be described. In the detector ring 12, for example, one unit ring 12a is formed by arranging ten radiation detectors 1 in an imaginary circle on a plane perpendicular to a z direction (vertical direction). For example, three unit rings 12a are arranged in the z direction to constitute the detector ring 12 (specifically, refer to FIG. 2).

Figure 3:
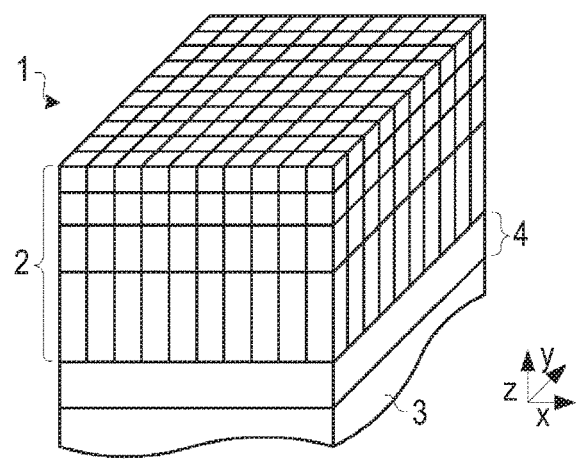
FIG. 3 is a perspective view for description of a radiation detector according to Embodiment 1.

A configuration of the radiation detector 1 will be briefly described. FIG. 3 is a perspective view for description of the configuration of the radiation detector 1 according to Embodiment 1. As illustrated in FIG. 3, the radiation detector 1 includes a scintillator 2 for converting radiation into light and a photodetector 3 having a silicon photomultiplier for detecting light. Further, a light guide 4 for exchanging light is provided at a position between the scintillator 2 and the photodetector 3.

The scintillator 2 is configured by three-dimensionally arranging scintillator crystals. A scintillator crystal includes $Lu_{2(1-X)}Y_{2X}SiO_5$ (hereinafter referred to as LYSO) in which Ce diffuses. Further, the photodetector 3 can specify a generation position of light corresponding to a scintillator crystal emitting light, and specify intensity of light and a time when light is generated. In addition, the scintillator 2 having the configuration of Embodiment 1 is merely an example of a mode that can be adopted. Therefore, a configuration of the invention is not limited thereto.

A detection signal output from the detector ring 12 is sent to the simultaneous counter 21 (see FIG. 1). Two γ-rays incident on the detector ring 12 at the same time correspond to an annihilation γ-ray pair caused by the radioactive drug in the subject. The simultaneous counter 21 counts the number of times that the annihilation γ-ray pair is detected for every two combinations in scintillator crystals included in the detector ring 12 and sends a result to the occurrence position specifying section 22. Time information assigned to detection signals by a clock is used for determination of simultaneity of the detection signals by the simultaneous counter 21. The occurrence position specifying section 22 corresponds to occurrence position specifying means of the invention.

Simultaneity for the simultaneous counter 21 does not mean complete coincidence of time. The simultaneous counter 21 recognizes two γ-rays incident on the detector ring 12 as an annihilation γ-ray pair even when detection times of the two γ-rays are slightly shifted. Some deviation is expected for a time at which the annihilation γ-ray pair is detected by the detector ring 12. The simultaneous counter 21 may reliably recognize the annihilation γ-ray pair by relaxing determination of simultaneity of γ-rays.

Figure 4:
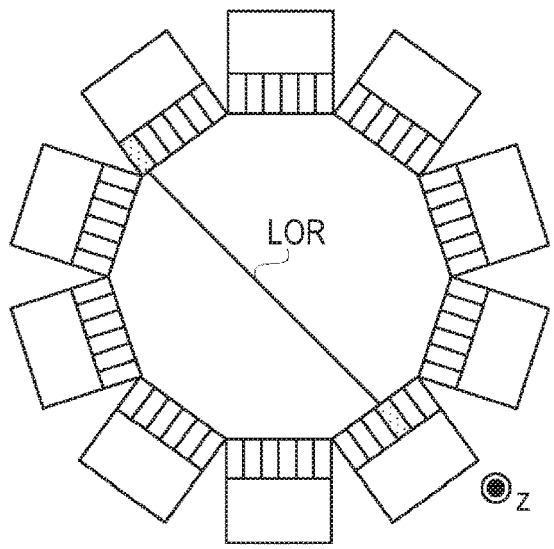
FIG. 4 is a schematic view for description of a line of response (LOR) according to Embodiment 1.

A description will be given of a reason for occurrence of a time difference in detection of the annihilation γ-ray pair. FIG. 4 illustrates a state in which the annihilation γ-ray pair is detected by the detector ring 12. Since the annihilation γ-ray pair travels in 180° opposite directions, when one of the pair travels in an upper left direction and enters a certain scintillator crystal, the other one of the pair travels in a lower right direction and enters another scintillator crystal. A line connecting these two scintillator crystals is referred to as an LOR, and the annihilation γ-ray pair is generated at a position on the line.

Figure 5:
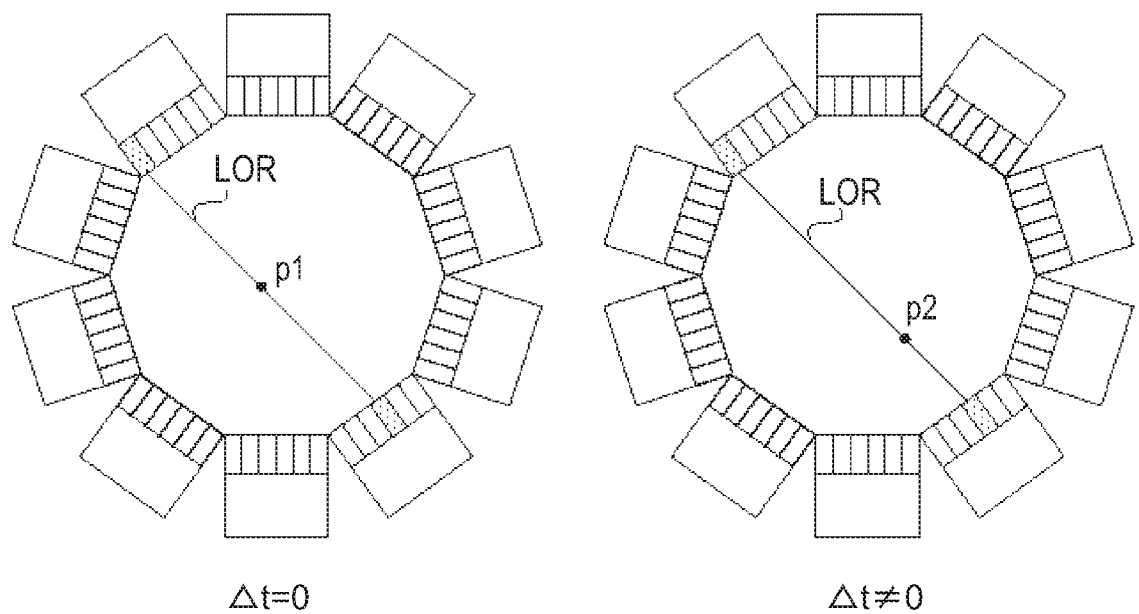
FIG. 5 is a schematic view for description of a time of flight (TOF) according to Embodiment 1.

A left side of FIG. 5 illustrates a case in which a time difference Δt related to detection of the annihilation γ-ray pair is 0. In this case, the annihilation γ-ray pair is generated at a midpoint p1 of the LOR. Since the annihilation γ-ray pair travels the same distance and enters the scintillator crystal, a time taken from occurrence to detection of the annihilation γ-ray pair is the same between the pair.

A right side of FIG. 5 illustrates a case in which the time difference Δt related to detection of the annihilation γ-ray pair is not 0. In this case, the annihilation γ-ray pair is generated at a point p2 away from a middle of the LOR. Since the annihilation γ-ray pair travels different distances and enters the scintillator crystal, there is a difference in the time taken from occurrence to detection of the annihilation γ-ray pair.

Due to such circumstances, the simultaneous counter 21 determines simultaneity of the γ-ray while allowing a certain time difference.

Such circumstances indicate that it is possible to specify an occurrence position of the annihilation γ-ray pair. In description of FIG. 4, the occurrence position of the annihilation γ-ray pair is present at a certain position on the LOR. However, it is possible to further narrow down the occurrence position of the annihilation γ-ray pair using a time difference in detection of the annihilation γ-ray pair. That is, when the time difference Δt related to detection of the annihilation γ-ray pair is 0, as illustrated on the left side of FIG. 5, it is found that the annihilation γ-ray pair is generated at the midpoint p1 of the LOR. In addition, for example, when the time difference Δt related to detection of the annihilation γ-ray pair is not 0, it is possible to detect the occurrence position of the annihilation γ-ray pair based on the magnitude of the time difference and a γ-ray detected earlier.

The radiation imaging apparatus according to Embodiment 1 is configured to detect the occurrence position of the annihilation γ-ray pair based on such an idea. An apparatus having such a configuration is referred to as a TOF-PET. The simultaneous counter 21 sends data related to coincidence to the occurrence position specifying section 22. The data related to coincidence does not merely mean a count number of the annihilation γ-ray pair, and includes individual information on each of the annihilation γ-ray pair. The occurrence position specifying section 22 specifies the occurrence position of the annihilation γ-ray pair based on the data related to coincidence. In this manner, the occurrence position specifying section 22 specifies an occurrence position of annihilation radiation based on a time difference when an annihilation radiation pair enters the detector ring 12 and an incident position of the annihilation radiation pair on the detector ring 12.

Figure 6:
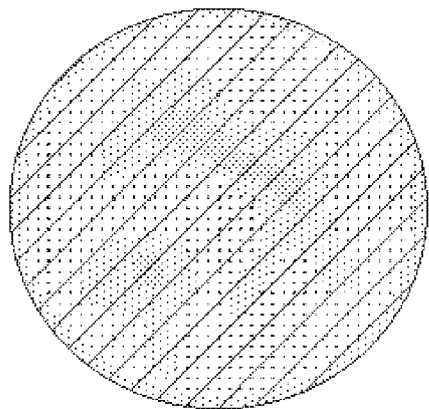
FIG. 6 is a schematic view for description of raw data according to Embodiment 1.

FIG. 6 illustrates a map in which a radioactive drug distribution is imaged based on the occurrence position of the annihilation γ-ray pair specified by the occurrence position specifying section 22. FIG. 6 maps concentration of the radioactive drug on a plane obtained by cutting the head of the subject in a round slice. Therefore, a part appearing to be a circle in FIG. 6 is a tomographic image of the head of the subject. In such a map, a distribution image of an absorption characteristic of a γ-ray indicated by oblique lines is superimposed on an image of a drug distribution indicated by shading. Only the drug distribution image indicated by shading is effective for diagnosis, and the absorption characteristic distribution image indicated by oblique lines interferes with accurate diagnosis.

In this regard, in the invention, as illustrated in FIG. 7, an absorption characteristic distribution indicated by oblique lines is extracted from output data of the occurrence position specifying section 22, and absorption correction is performed based thereon, thereby obtaining a drug distribution image indicated by shading. Conventional absorption correction is configured to obtain an absorption characteristic distribution indicated by oblique lines using another imaging. A greatest feature of the invention is a configuration in which an absorption characteristic distribution is extracted from output data of the occurrence position specifying section 22.

Raw data output from the occurrence position specifying section 22 is sent to the outline extracting section 23. As illustrated in FIG. 8, the outline extracting section 23 recognizes an outline of the subject from raw data illustrated in FIG. 6. As an outline recognition scheme, a map illustrated in FIG. 6 may be generated from raw data, and an outline may be recognized by image recognition. Alternatively, an outline may be recognized by comparing count numbers of LORs parallel to each other and included in raw data. Since the head of the subject is located at a center of a field of view of the detector ring 12, the head of the subject is not present at a circumference of the field of view. Therefore, when the count numbers of the LORs parallel to each other are examined in order from an LOR at one end of the field of view toward an LOR at the other end, a first LOR is located at the circumference of the field of view, and thus radiation detection is not present. When each LOR is examined therefrom toward the center of the field of view, the LOR approaches the head of the subject, and the count number abruptly increases. Based on such a principle, the outline extracting section 23 may recognize the outline of the subject by searching for an LOR whose count number abruptly increases in the LORs parallel to each other.

A capillary vessel in which the radioactive drug is easily collected is present in an outline part of the subject. Therefore, in the map described with reference to FIG. 6, a radioactive drug accumulated in the capillary vessel appears at relatively high concentration. The outline extracting section 23 may extract the outline of the subject from the raw data using such a characteristic.

Data indicating a position of the outline of the subject in the field of view generated by the outline extracting section 23 is sent to the data selecting section 24. The data selecting section 24 selects data related to detection of radiation emitted from the outline of the subject from raw data output from the occurrence position specifying section 22, and generates new data. As illustrated in FIG. 9, the raw data may be considered as data in which the LOR is associated with the count number. The data selecting section 24 selects only data related to detection of radiation emitted from the outline of the subject from such raw data, and generates selection data. That is, the data selecting section 24 selects data on a pair generated in the vicinity of the surface of the subject from data indicating the generation position of radiation specified by the occurrence position specifying section 22. The data selecting section 24 corresponds to data selecting means of the invention.

Figure 10:
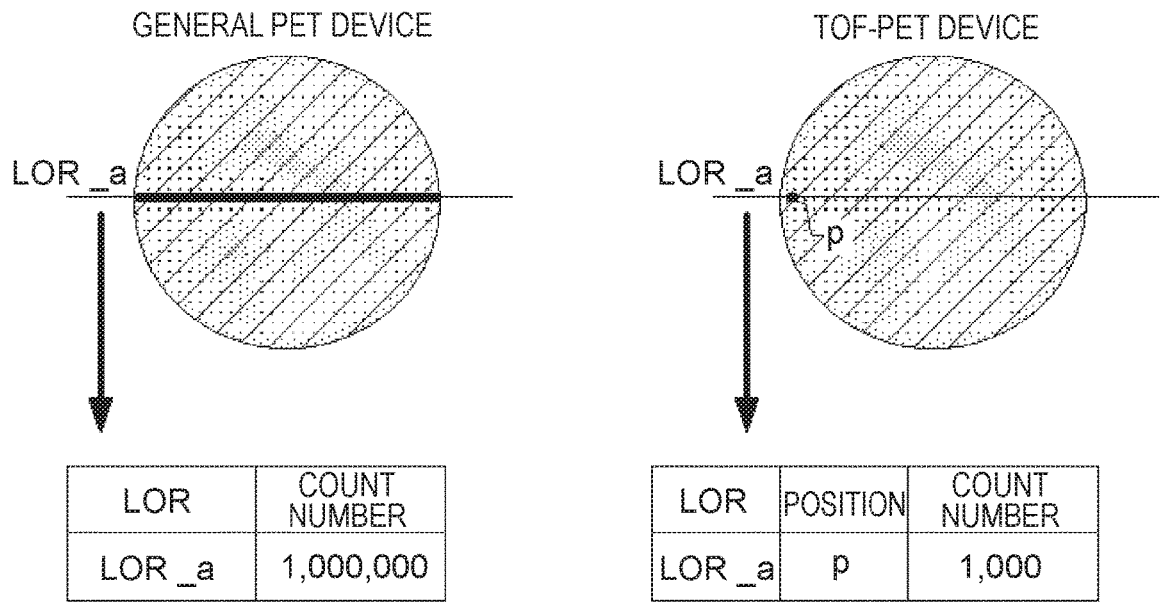
FIG. 10 is a schematic view for description of a characteristic of raw data according to Embodiment 1.

It should be noted that such data selection is possible since the TOF-PET is adopted. FIG. 10 describes such circumstances. A left side of FIG. 10 illustrates a scheme in which a count number related to a certain LOR (LOR_a) is described in raw data. The raw data in this case refers to an output of the simultaneous counter 21 and does not refer to an output of the occurrence position specifying section 22 specific to the TOF-PET. As can be seen from the left side of FIG. 10, a count of LOR_a is merely described in the raw data. Therefore, for example, even when one million counts are detected for LOR_a, it is impossible to detect a position on the LOR from which each count occurs. Therefore, in the raw data, on the left side of FIG. 10, detection of radiation generated from somewhere in a range indicated by a bold line on LOR_a is treated together. Nonetheless, since it is clear that the annihilation radiation pair is generated in the subject, radiation related to the count for LOR_a has occurred somewhere in the subject.

In comparison, TOF_PET in this specification can classify one million counts of radiation observed on LOR_a in more detail. That is, according to the principle described in FIG. 5, the apparatus of this specification can detect a count for a point p on LOR_a out of one million counts. In FIG. 10, the count for the point p on LOR_a corresponds to 1,000. It is presumed that the point p is located at the outline of the subject.

Figure 11:
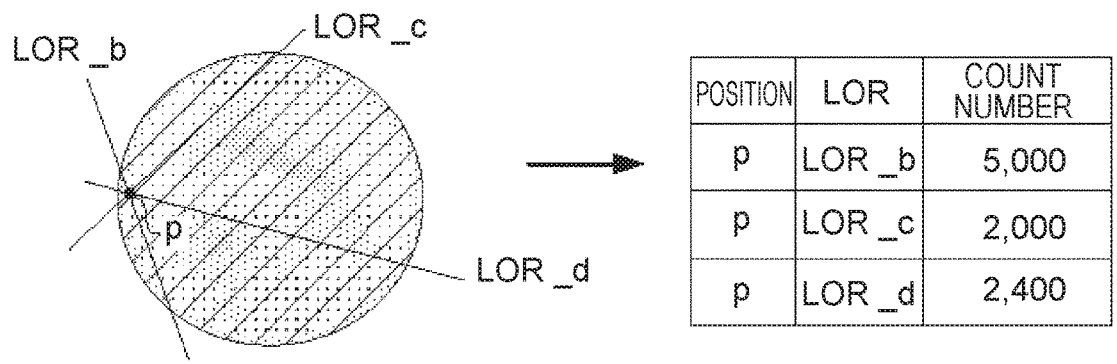
FIG. 11 is a schematic view for description of the data selection process according to Embodiment 1.

Naturally, not only LOR_a corresponds to an LOR passing through the point p. In FIG. 11, three LORs of LOR_b, LOR_c, and LOR_d passing through the point p are drawn. Since these LORs are described in the raw data, similarly to LOR_a, a count for the point p on each LOR can be detected.

The data selecting section 24 of the invention extracts a detection count of radiation for each LOR passing through the point p located on the outline of the subject from original data based on such a principle. It is possible to easily detect a position in the field of view corresponding to the outline of the subject from data output by the outline extracting section 23. Data selected by the data selecting section 24 is related to the annihilation radiation pair derived from the radioactive drug accumulated in the capillary vessel under a skin of the subject as described with reference to FIG. 6.

Data indicating the count number of radiation for the point p is sent to the absorption characteristic distribution-computing section 25. The data sent at this time is data in which the LOR is associated with the count number, and the count number is counted with respect to radiation generated at the point p. The absorption characteristic distribution-computing section 25 corresponds to absorption characteristic distribution computing means of the invention.

Figure 12:
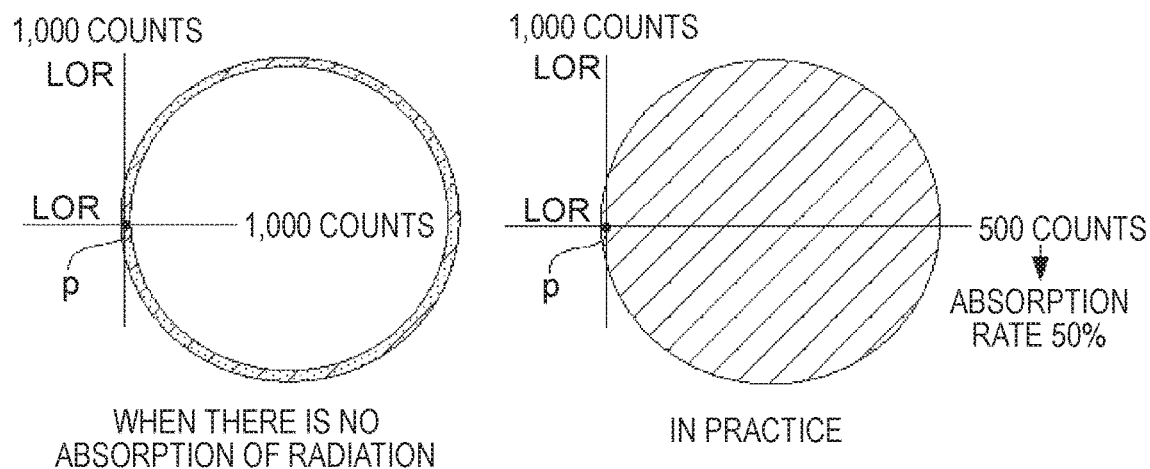
FIG. 12 is a schematic view for description of an absorption characteristic distribution computation process according to Embodiment 1.

As illustrated in FIG. 12, two LORs passing through the point p are considered. One of the LORs extends in a tangential direction of the outline of the subject in a shape of a closed loop, and the other one is an LOR penetrating the inside of the subject. For convenience of description, it is presumed that the two LORs are orthogonal to each other.

Since radiation generated at the point p is radiated in all directions, there should be no bias in a direction of scattering. That is, as illustrated in FIG. 12, among radiation rays radiated from the point p, the number of radiation rays directed in the tangential direction of the outline should be the same as the number of radiation rays directed in a direction orthogonal to the tangential direction. Therefore, as illustrated on a left side of FIG. 12, when a count number for the LOR in the tangential direction is 1000 counts, a count number of the LOR in the orthogonal direction should be 1000 counts. Further, since the LOR in the orthogonal direction penetrates through a subject image, radiation derived from a right end of the outline illustrated on the left side of FIG. 12 should be detected in the detector ring 12. However, since the apparatus according to the invention is the TOF-PET, it is possible to detect a count number for only the point p positioned at a left end of the outline.

However, in practice, the count numbers of the two LORs are not the same since there is bias in absorption of radiation emitted from the point p. A right side of FIG. 12 describes such circumstances. Not all radiation rays generated at the point p reach the detector ring 12 since radiation absorption occurs in the subject. For this absorption, first, LOR in the tangential direction is considered. Radiation generated at the point p to scatter in the tangential direction of the outline of the subject is extracted from the subject immediately after generation. Therefore, the radiation scattering in the tangential direction is detected by the detector ring 12 almost without being absorbed by the subject.

The above description is not applied to radiation scattering along the LOR in orthogonal direction. Radiation generated at the point p to scatter in orthogonal direction orthogonal to the tangential direction needs to cross the inside of the subject for a long distance before reaching the detector ring 12. A part of the radiation is absorbed as the radiation passes through the subject, and not all the radiation reaches the detector ring 12. Therefore, as illustrated on the right side of FIG. 12, when the count number for the LOR in the tangential direction is 1000 counts, the count number of the LOR in the orthogonal direction is smaller than 1000, for example 500 counts. Radiation generated at the point p to scatter along the LOR in the orthogonal direction has two types of radiation corresponding to radiation scattering toward the right side of the point p and radiation scattering toward the left side. One of the two types of radiation scattering toward the left side immediately escapes the subject, and thus enters the detector ring 12 almost without being absorbed. However, the simultaneous counter 21 counts the detection number of the radiation when both the radiation scattering toward the right side and the radiation scattering toward the left side are detected. Therefore, the count of the annihilation radiation pair decreases as the radiation scattering toward the right side of the point p is absorbed.

A degree of absorption of the radiation scattering along the LOR in the orthogonal direction can be found by comparing the count number related to the LOR in the orthogonal direction with the count number for the LOR in the tangential direction since the count number for the LOR in the tangential direction can be considered as a criterion not affected by radiation absorption. In the case of the right side of FIG. 12, the count number in the absence of radiation absorption in the subject may be considered to be 1000 which is the same as the count number related to the LOR in the tangential direction. Since the count number of the LOR in the orthogonal direction is 500, which is half a count number in the case in which there is no absorption, it can be understood that a radiation absorption rate for LOR in the orthogonal direction is 50%.

Figure 13:
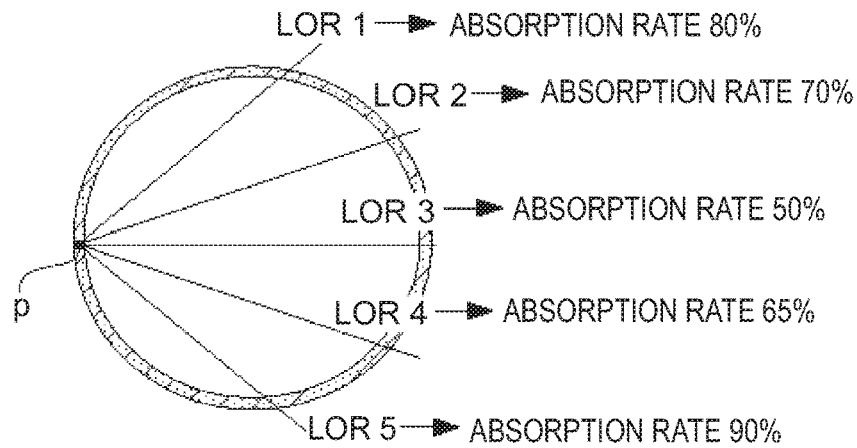
FIG. 13 is a schematic view for description of the absorption characteristic distribution computation process according to Embodiment 1.

When a difference in the count number seen between different LORs is examined, it is possible to detect an absorption characteristic of the entire inside of the subject. FIG. 13 illustrates a state in which an absorption rate is computed for each of a plurality of LOR1 to LOR5 passing through the point p. Computation of all of these absorption rates is based on the count number related to the LOR in the tangential direction. The absorption characteristic distribution-computing section 25 repeats computation of the absorption rate related to the point p based on such a principle.

Figure 14:
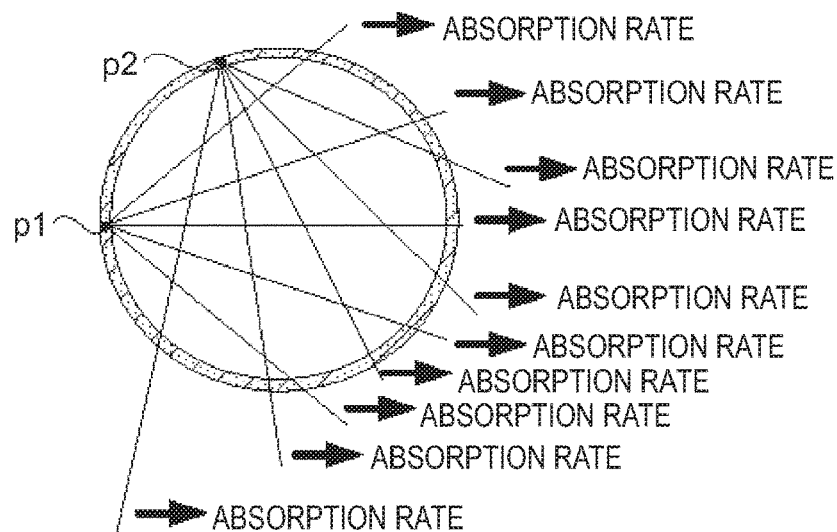
FIG. 14 is a schematic view for description of the absorption characteristic distribution computation process according to Embodiment 1.

FIG. 14 illustrates a state of computing absorption rates related to LORs for a point p1 and a point p2 different from the point p belonging to the outline of the subject. The absorption characteristic distribution-computing section 25 repeats computation of the absorption rates related to the point p1 and the point 2 based on the same principle as that described with respect to the point p. The absorption characteristic distribution-computing section 25 completes computation of absorption rates for all points belonging to the outline of the subject in this manner. That is, the absorption characteristic distribution-computing section 25 operates by computing an absorption rate of radiation by dividing the number of times of detection of a pair scattering in a tangential direction of a curved surface forming the surface of the subject by the number of times of detection of a pair scattering in a direction of penetrating through the subject.

Figure 15:
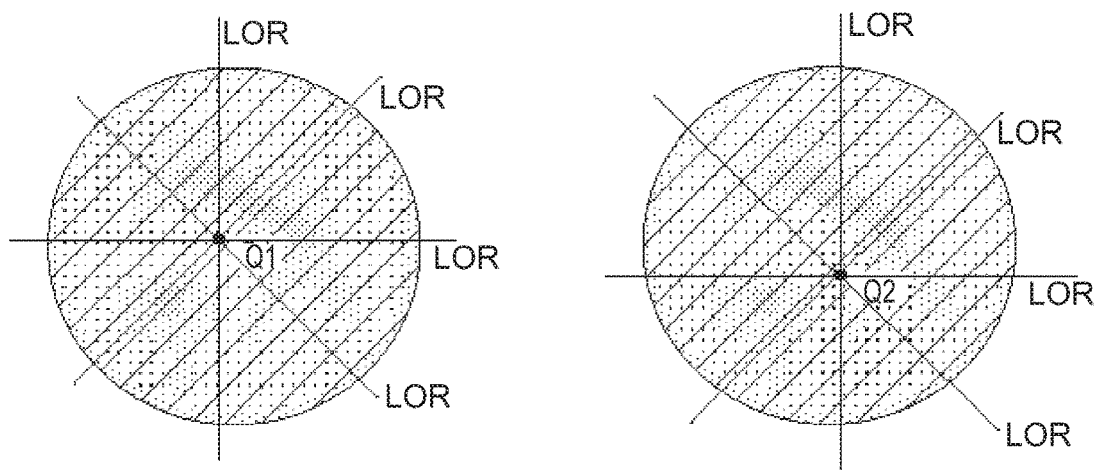
FIG. 15 is a schematic view for description of the absorption characteristic distribution computation process according to Embodiment 1.

FIG. 15 illustrates a state in which an absorption characteristic in the subject is mapped based on an absorption rate obtained in this way. FIG. 15 illustrates a state of computing an absorption characteristic of radiation for a point located inside the subject. A description will be given of a point Q1 on a left side of FIG. 15. All LORs passing through the point Q1 pass through the outline of the subject. Since computation of the absorption rate described with reference to FIG. 14 has been performed for all points belonging to the outline of the subject by the absorption characteristic distribution-computing section 25, the absorption rate has already been computed for all these LORs. Since all the LORs shown on the left side of FIG. 15 pass through the point Q1, when the point Q1 is a part which is likely to absorb radiation, the absorption rate should be low. This situation is similarly applied to a point Q2 close to the point Q1.

Figure 16:
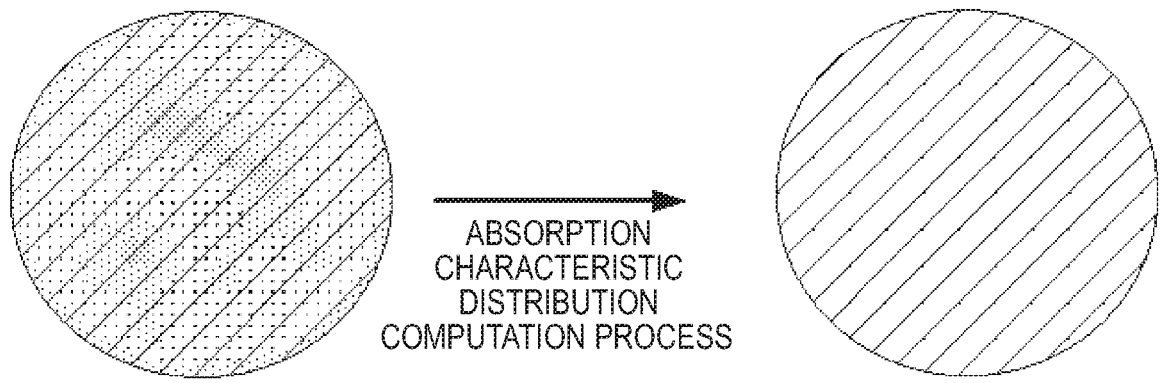
FIG. 16 is a schematic view for description of the absorption characteristic distribution computation process according to Embodiment 1.

For example, the absorption characteristic distribution-computing section 25 may evaluate a difference in absorption characteristic of radiation between respective points by computing an average value of absorption rates related to LORs passing through the point Q1 and an average value of absorption rates related to LORs passing through the point Q2. In FIG. 15, only the two points Q1 and Q2 in the subject are considered as a problem. However, when the average value is computed for all the points included in the subject, comparison of absorption characteristics of radiation can be performed in the entire area of the subject. Based on such a principle, as illustrated in FIG. 16, the absorption characteristic distribution-computing section 25 computes a distribution of radiation absorption characteristics inside the subject, and computes data indicating the distribution of the radiation absorption characteristics inside the subject from original data. In FIG. 16, for the sake of simplicity, data is drawn as a tomographic image. However, actual data is a data set in which a position and intensity are associated with each other.

As described above, based on the number of times of detection of radiation scattering in the tangential direction of the curved surface forming the surface of the subject in the annihilation radiation pair derived from the vicinity of the surface of the subject based on selected data, the absorption characteristic distribution-computing section 25 computes absorption characteristic distribution data indicating a distribution of absorption characteristics of annihilation radiation inside the subject by computing a level of decrease of the number of times of detection of one of the pair scattering in the direction of penetrating the subject due to absorption in the subject.

Figure 17:
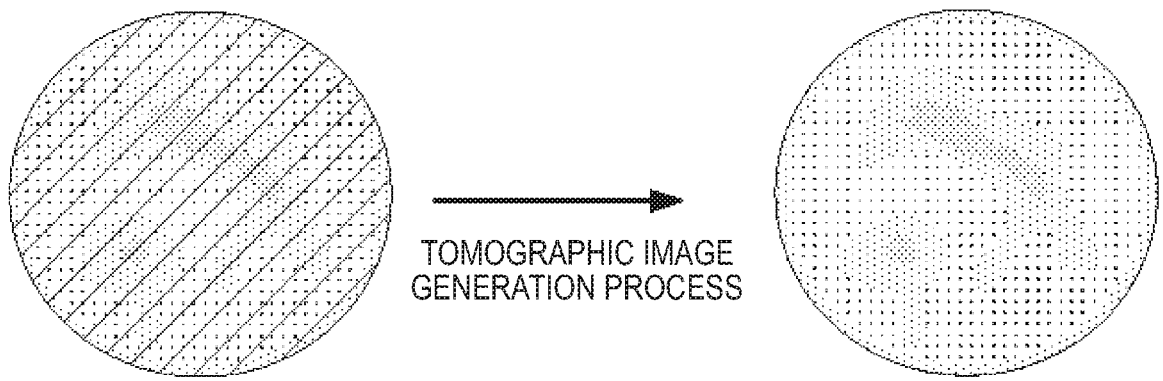
FIG. 17 is a schematic view for description of a tomographic image generation process according to Embodiment 1.

Data indicating a distribution of radiation absorption characteristics is sent to the tomographic image generating section 26. As illustrated in FIG. 17, the tomographic image generating section 26 generates a tomographic image indicating only a radioactive drug distribution inside the subject by eliminating an influence of radiation absorption inside the subject based on the data indicating the distribution of radiation absorption characteristics from raw data output by the occurrence position specifying section 22. The tomographic image generating section 26 generates an image indicating a radioactive drug distribution inside the subject based on data indicating an occurrence position of radiation specified by the occurrence position specifying section 22. In this instance, the tomographic image generating section 26 generates the image by executing absorption correction based on absorption characteristic distribution data. The tomographic image generating section 26 corresponds to tomographic image generating means of the invention.

A main controller 31 is configured to execute a program for implementing the respective sections 21, 22, 23, 24, 25, and 26. The memory 32 is configured to store parameters necessary for operation of the respective sections 21, 22, 23, 24, 25, and 26 and intermediate data generated by various computations. The console 33 is configured to allow an operator to input instructions such as start of detection. A display 34 is configured to display a tomographic image.

As described above, according to the invention, it is possible to realize both reduction of manufacturing cost of the PET device and reduction of a burden on the subject by simultaneously performing acquisition of transmission data and measurement of the annihilation radiation pair using the single detector ring 12. The radiation imaging apparatus according to the invention is a TOF-PET, and may specify an occurrence position of annihilation radiation based on a time difference when an annihilation radiation pair enters the detector ring 12. The invention utilizes such a characteristic of the TOF-PET.

A greatest feature of the invention is to compute absorption characteristic distribution data (transmission data) indicating a distribution of absorption characteristics of annihilation radiation inside the subject from data on an annihilation radiation pair derived from the vicinity of the surface of the subject. In the TOF-PET, an occurrence position of a detected annihilation radiation pair is known, and thus it is possible to select data on the pair.

Conventional transmission data acquisition is performed by inserting a radiation source (external source) into a gap formed between the detector ring 12 and the subject and transmitting radiation to the subject. The inventor of the invention thought that a radioactive drug administered to the subject could replace this radiation source without being bound by such technical common sense. The radioactive drug travels around the whole body of the subject, and thus is distributed to some extent on the surface of the subject. In this regard, an idea of using the radioactive drug accumulated on the surface of this subject in place of the conventional external source has been created.

According to the invention, since transmission data can be obtained by detection of the radioactive drug derived from the subject, imaging exclusively for transmission data is unnecessary. In this way, the detector ring 12 dedicated to transmission data is not required, and it is unnecessary to take time for imaging exclusively for transmission data.

In addition, according to the invention, it is possible to obtain transmission data more suitable for absorption correction. In a conventional method using the external source, it is impossible to obtain transmission data faithfully representing an absorption distribution of a radioactive drug since energy of radiation emitted from the external source is different from energy of radiation emitted from the radioactive drug. According to the invention, transmission data is acquired by radiation derived from the radioactive drug, and thus it is possible to compute transmission data more faithfully showing a scheme in which radiation derived from the radioactive drug is absorbed.

Embodiment 2

Figure 18:
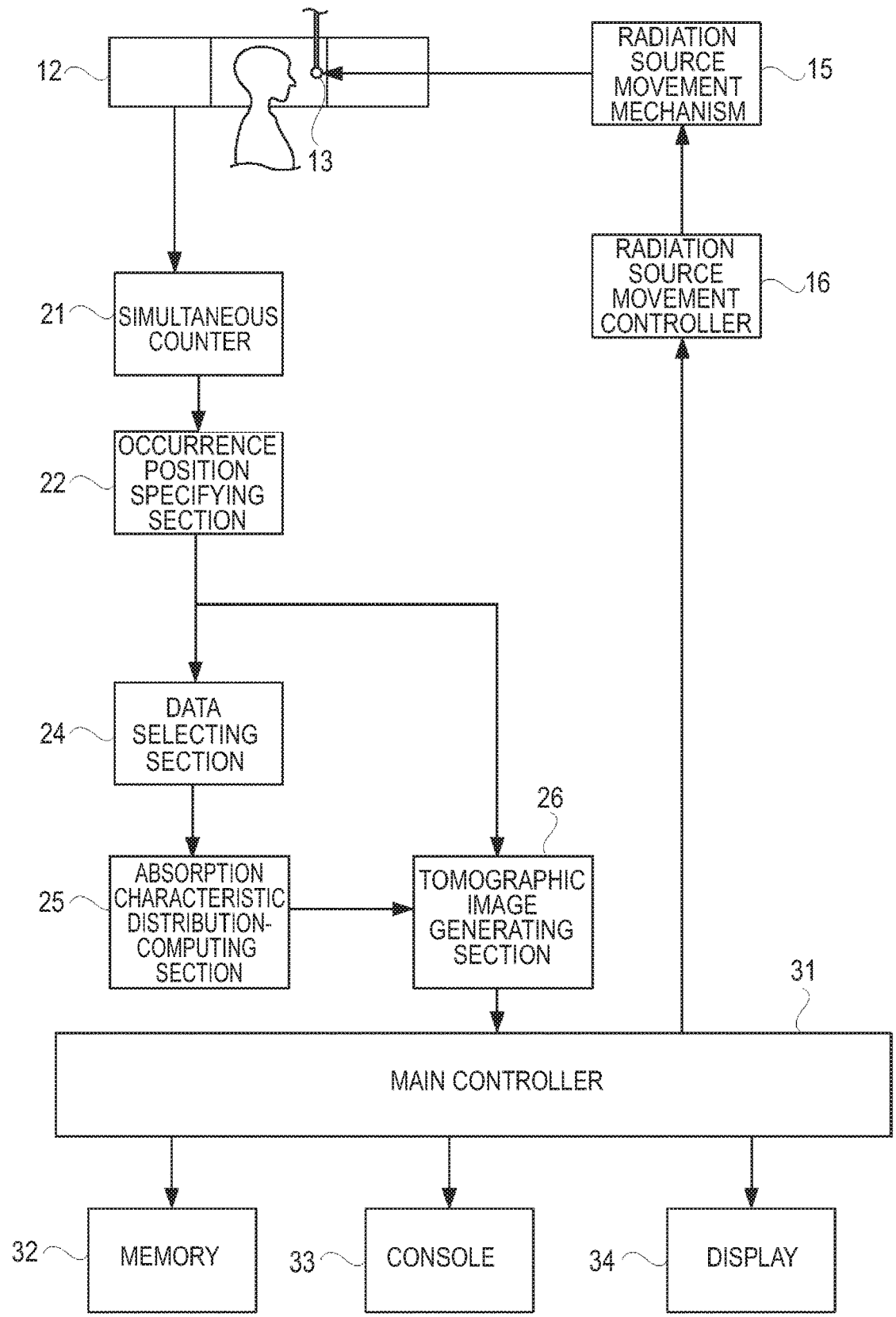
FIG. 18 is a functional block diagram for description of a radiation tomograph according to Embodiment 2.

Next, a description will be given of a radiation tomograph according to Embodiment 2. The radiation tomograph according to Embodiment 2 is greatly different from the configuration of Embodiment 1 in that a radiation source 13 is included inside a detector ring 12 as illustrated in FIG. 18. In Embodiment 2, the outline extracting section 23 may not be used.

Figure 19:
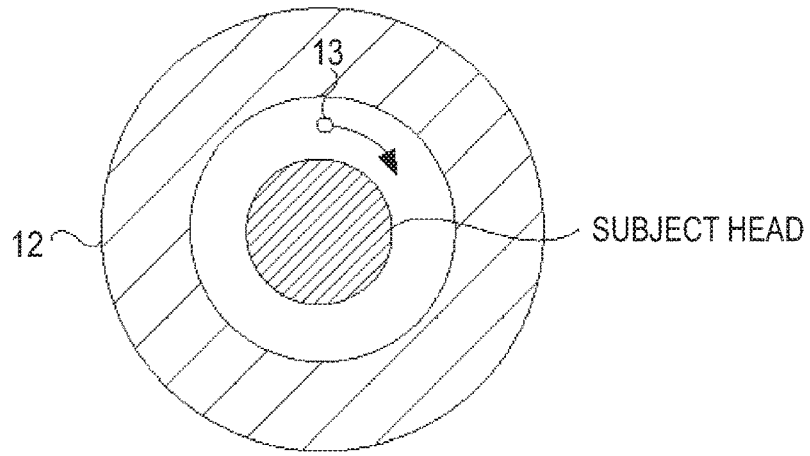
FIG. 19 is a plan view for description of movement of a radiation source according to Embodiment 2.

The radiation source 13 is a point radiation source in which radioactive cesium emitting radiation of 662 kev is enclosed. The radiation source 13 is supported by a support extending parallel to a central axis of the detector ring 12, and the support is connected to a radiation movement mechanism 15. As illustrated in FIG. 19, the radiation source 13 is configured to make one round around the head of the subject using the radiation source movement mechanism 15. A radiation source movement controller 16 is configured to control the radiation source movement mechanism 15. The radiation source 13 is configured to irradiate radiation from the outside of the subject, and is disposed in the detector ring 12.

Figure 20:
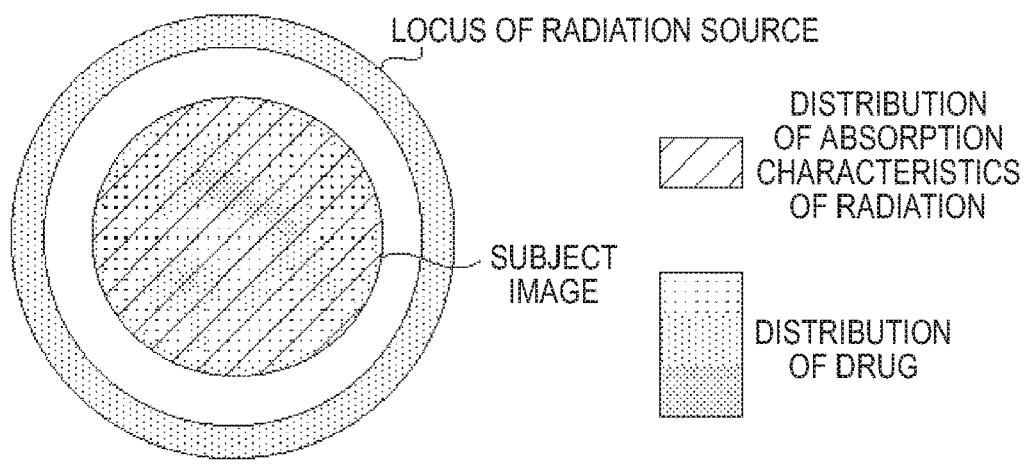
FIG. 20 is a schematic view for description of raw data according to Embodiment 2.

In the apparatus according to Embodiment 2, radiation is detected while rotating the radiation source 13 with respect to the subject. Therefore, in the apparatus of Embodiment 2, raw data output by an occurrence position specifying section 22 includes a donut-shaped image corresponding to a locus of the radiation source 13 as illustrated in FIG. 20.

A data selecting section 24 selects data related to detection of radiation emitted by the radiation source 13 from raw data output by the occurrence position specifying section 22, and generates new data. As illustrated in FIG. 9, the raw data may be considered to be data in which an LOR is associated with a count number. The data selecting section 24 selects only data related to detection of radiation emitted by the radiation source 13 from such raw data, and generates selection data. As described with reference to FIG. 10, it should be noted that such data selection is possible since the TOF-PET is adopted. It is possible to easily detect a position in a field of view corresponding to a locus of the radiation source 13 based on a positional relationship between the radiation source 13 and the detector ring 12 and a movement mode of the radiation source 13. The data selecting section 24 selects data on a pair generated by the radiation source 13 from data indicating an occurrence position of radiation specified by the occurrence position specifying section 22.

Figure 21:
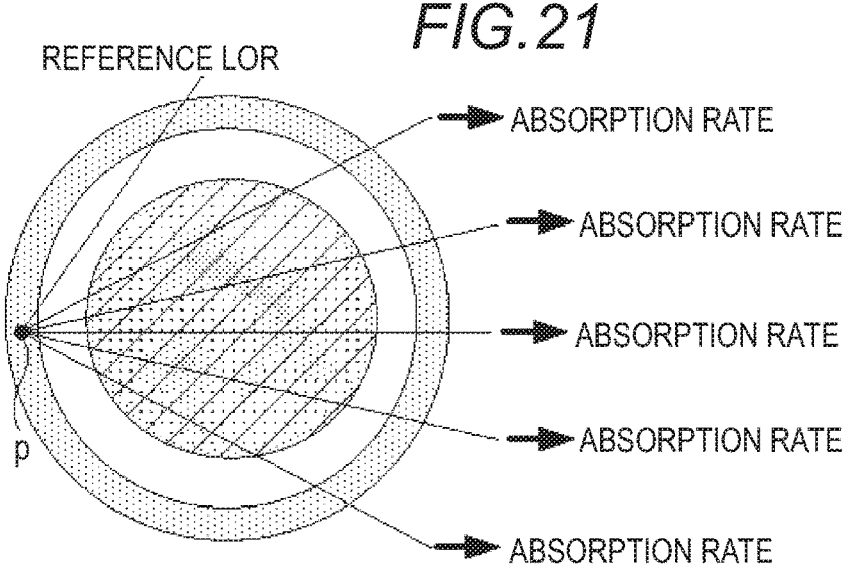
FIG. 21 is a schematic view for description of an absorption characteristic distribution computation process according to Embodiment 2.
Figure 22:
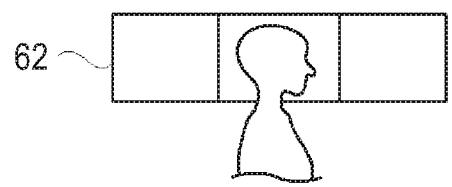
FIG. 22 is a schematic view for description of a PET device for heads according to a conventional configuration.

The data selecting section 24 sends the selection data to an absorption characteristic distribution-computing section 25. Therefore, data indicating a count number of radiation for a point p belonging to the locus of the radiation source 13 in FIG. 21 is sent to the absorption characteristic distribution-computing section 25 at this time. The data to be sent is data in which the LOR is associated with the count number, and the count number is counted with respect to radiation generated at the point p. The absorption characteristic distribution-computing section 25 computes absorption characteristic distribution data indicating a distribution of absorption characteristics of annihilation radiation in the subject based on the selected data.

As illustrated in FIG. 21, LORs passing through the point p is considered. One of the LORs directly enters the detector ring 12 without passing through the subject, and the others are LORs penetrating the inside of the subject.

Since radiation generated at the point p is radiated in all directions, there should be no bias in a direction of scattering. However, in practice, count numbers of LORs are not the same since there is bias in absorption of radiation emitted from the point p. Radiation generated at the point p to enter the detector ring 12 without passing through the subject is detected by the detector ring 12 without being absorbed by the subject.

However, the above description is not applied to radiation scattering along an LOR penetrating the inside of the subject. This radiation needs to cross the inside of the subject before reaching the detector ring 12. A part of the radiation is absorbed as the radiation passes through the subject, and not all the radiation reaches the detector ring 12.

A degree of absorption of radiation scattering along an LOR in the orthogonal direction can be found by comparing a count number related to an LOR not passing through the subject with a count number with regard to an LOR passing through the subject since the count number with regard to the LOR not passing through the subject may be considered as a criterion not affected by radiation absorption.

When a difference in the count number seen between different LORs is examined, it is possible to detect an absorption characteristic of the entire inside of the subject. FIG. 21 illustrates a state in which an absorption rate is computed for each of a plurality of LORs passing through the point p. Computation of all of these absorption rates is based on the count number related to the LOR not passing through the subject. The absorption characteristic distribution-computing section 25 repeats computation of the absorption rate related to the point p based on such a principle.

The absorption characteristic distribution-computing section 25 repeats computation of an absorption rate for another point on the locus of the radiation source 13 based on the same principle as that described with regard to the point p of FIG. 21. The absorption characteristic distribution-computing section 25 completes computation of absorption rates for all points belonging to the locus of the radiation source 13 in this manner.

It is possible to map an absorption characteristic in the subject based on the absorption rate obtained in this way. This point has been described with reference to FIG. 15. That is, for example, the absorption characteristic distribution-computing section 25 may evaluate a difference in absorption characteristic of radiation between respective points by computing an average value of absorption rates related to LORs passing through a certain point Q1 and an average value of absorption rates related to LORs passing through another point Q2. When an average value is computed for all points included in the subject, comparison of absorption characteristics of radiation may be performed in the entire area in the subject. The absorption characteristic distribution-computing section 25 computes a distribution of radiation absorption characteristics in the subject, and computes data indicating a distribution of radiation absorption characteristics in the subject from original data based on such principle. Data obtained at this time is a data set in which a position is associated with intensity.

The data indicating the distribution of the radiation absorption characteristics is sent to a tomographic image generating section 26. The tomographic image generating section 26 generates a tomographic image indicating only a radioactive drug distribution inside the subject by eliminating an influence of radiation absorption inside the subject based on the data indicating the distribution of radiation absorption characteristics from raw data output by the occurrence position specifying section 22. This operation is the same as that in Embodiment 1.

As described above, another configuration in the invention is described as a configuration of Embodiment 2. According to this configuration, it is possible to realize both reduction of manufacturing cost of the PET device and reduction of a burden on the subject by simultaneously performing acquisition of transmission data and measurement of the annihilation radiation pair using the single detector ring 12.

The radiation imaging apparatus according to the invention is a TOF-PET, and may specify an occurrence position of annihilation radiation based on a time difference when an annihilation radiation pair enters the detector ring 12. The invention utilizes such a characteristic of the TOF-PET.

Conventional transmission data acquisition is performed by inserting a radiation source (external source) into a gap formed between the detector ring 12 and the subject and transmitting radiation to the subject. Thereafter, the external source is separated from the detector ring 12, and detection of radiation derived from the radioactive drug distributed in the subject is performed this time to acquire emission data. The inventor of the invention thought whether not only transmission data but also emission data can be obtained in a state in which the external source is introduced without being bound by such technical common sense.

According to the invention, there is provided a data selecting section 24 capable of separating data related to radiation derived from the external source from data detected by the detector ring 12 and generating transmission data. The data detected by the detector ring 12 includes data on radiation derived from the radioactive drug in the subject. Therefore, when absorption correction using transmission data is performed on this data, it is possible to obtain a radioactive drug distribution image from which the absorption characteristic of the subject is eliminated.

According to the invention, it is possible to obtain a distribution image only by imaging using the external source without performing imaging twice under different conditions of having and not having the external source.

The invention is not limited to the above-described embodiment, and may be modified as follows.

(1) The outline extracting section 23 of Embodiment 1 extracts the outline of the subject from the raw data output from the occurrence position specifying section 22. However, the invention is not limited to this configuration. Instead of the raw data, the outline extracting section 23 may extract the outline of the subject based on a tomographic image obtained by CT imaging or MRI imaging in the past. The outline of the subject maintains comparatively the same shape even after years elapse. Therefore, PET imaging according to the invention may be executed with reference to a previously captured CT image, etc. The data selecting section 24 according to the present modification operates based on data indicating a shape of the outline of the subject which is acquired in advance.

(2) An image processing apparatus according to the invention can be realized by executing the following process. That is, in the process, software (program) for realizing functions of the above-described embodiments is supplied to a system or apparatus via a network or various storage media, and a computer (or a CPU, an MPU, etc.) of the system or apparatus reads and executes the program.

Figure 23:
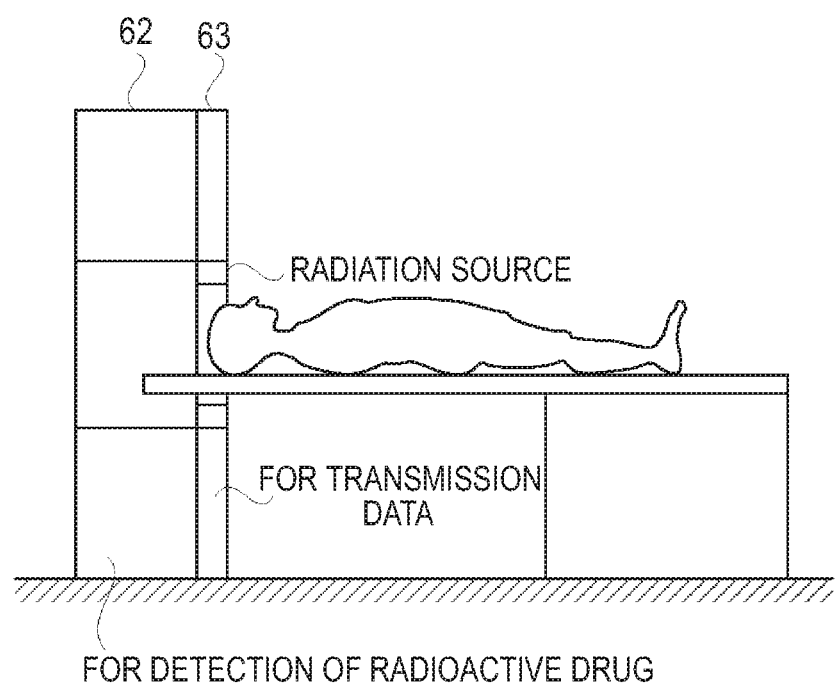
FIG. 23 is a schematic view for description of a PET device for heads according to a conventional configuration.

(3) The invention according to Embodiment 2 can be realized using a radiation source on a ring as described with reference to FIG. 23 in place of the radiation source 13 serving as a point source.

(4) Even though the PET device for heads has been mainly described in this specification, the invention may be applied to another PET device such as a PET device for a whole body, a PET device for breast examination, etc.

The invention claimed is:

1. An information processing apparatus mounted in a radiation tomograph including a detector ring for detecting an annihilation radiation pair derived from a radioactive drug distributed in a subject, the information processing apparatus comprising:
occurrence position specifying means for specifying an occurrence position of annihilation radiation based on a time difference when an annihilation radiation pair enters the detector ring and an incident position of the annihilation radiation pair on the detector ring;
data selecting means for selecting data on a pair generated in a vicinity of a surface of the subject from data indicating an occurrence position of radiation specified by the occurrence position specifying means;
absorption characteristic distribution computing means for computing absorption characteristic distribution data indicating a distribution of absorption characteristics of annihilation radiation inside the subject by computing a level of decrease of the number of times of detection of one of a pair scattering in a direction of penetrating the subject due to absorption in the subject based on the number of times of detection of radiation scattering in a tangential direction of a curved surface forming the surface of the subject in an annihilation radiation pair derived from the vicinity of the surface of the subject based on selected data; and
image generating means for generating an image indicating a radioactive drug distribution in the subject based on data indicating an occurrence position of radiation specified by the occurrence position specifying means,
wherein the image generating means generates an image by executing absorption correction based on the absorption characteristic distribution data.

2. The information processing apparatus according to claim 1, wherein data selected by the data selecting means is related to an annihilation radiation pair derived from a radioactive drug accumulated in a capillary vessel under a skin of the subject.

3. The information processing apparatus according to claim 1, wherein the absorption characteristic distribution computing means operates by computing an absorption rate of radiation by dividing the number of times of detection of a pair scattering in the tangential direction of the curved surface forming the surface of the subject by the number of times of detection of a pair scattering in a direction of penetrating through the subject.

4. The information processing apparatus according to claim 1, wherein the data selecting means operates based on data indicating a shape of an outline of the subject acquired in advance.

5. A memory storing a program causing a computer to function as each means of the information processing apparatus according to claim 1.

6. A radiation imaging apparatus comprising the information processing apparatus according to claim 1.

7. The radiation imaging apparatus according to claim 6, wherein the radiation imaging apparatus is used for head imaging.

8. An information processing apparatus mounted in a radiation tomograph including a detector ring for detecting an annihilation radiation pair derived from a radioactive drug distributed in a subject and a radiation source configured to irradiate radiation from an outside of the subject and disposed inside the detector ring, the information processing apparatus comprising:
occurrence position specifying means for specifying an occurrence position of annihilation radiation based on a time difference when an annihilation radiation pair enters the detector ring and an incident position of the annihilation radiation pair on the detector ring;
data selecting means for selecting data on a pair generated by the radiation source from data indicating an occurrence position of radiation specified by the occurrence position specifying means;
absorption characteristic distribution computing means for computing absorption characteristic distribution data indicating a distribution of absorption characteristics of annihilation radiation in the subject based on selected data; and
image generating means for generating an image indicating a radioactive drug distribution in the subject based on data indicating an occurrence position of radiation specified by the occurrence position specifying means,
wherein the image generating means generates an image by executing absorption correction based on the absorption characteristic distribution data.

* * * * *